(12) United States Patent
Flanagan

(10) Patent No.: US 10,350,040 B1
(45) Date of Patent: Jul. 16, 2019

(54) WEDGE DEVICE FOR FACILITATING TREATMENT OF INTERPROXIMAL DENTAL CARIES, AND METHOD OF USE

(71) Applicant: Dennis F. Flanagan, Mystic, CT (US)

(72) Inventor: Dennis F. Flanagan, Mystic, CT (US)

(*) Notice: Subject to any disclaimer, the term of this patent is extended or adjusted under 35 U.S.C. 154(b) by 0 days.

(21) Appl. No.: 15/984,329

(22) Filed: May 19, 2018

(51) Int. Cl.
  *A61C 5/00* (2017.01)
  *A61C 19/06* (2006.01)
  *A61C 5/88* (2017.01)

(52) U.S. Cl.
  CPC .............. *A61C 19/063* (2013.01); *A61C 5/88* (2017.02)

(58) Field of Classification Search
  CPC ..... A61C 15/02; A61C 15/043; A61C 15/046; A61C 17/227; A61C 17/0205; A61C 19/063; A61C 5/88
  See application file for complete search history.

(56) References Cited

U.S. PATENT DOCUMENTS

| | | | | |
|---|---|---|---|---|
| 719,017 | A * | 1/1903 | Lenhardtson | A61C 15/02 132/328 |
| 1,624,054 | A * | 4/1927 | Kuhne | A61C 15/00 132/329 |
| 2,510,194 | A * | 6/1950 | Thomas | A61C 15/02 132/325 |
| 3,199,510 | A * | 8/1965 | Sinai | A61C 17/02 128/200.14 |
| 3,943,628 | A * | 3/1976 | Kronman | A61C 3/00 433/89 |
| 4,913,176 | A * | 4/1990 | DeNiro | A61C 15/02 132/329 |
| 5,030,093 | A * | 7/1991 | Mitnick | A61C 3/005 250/504 H |
| 5,890,630 | A * | 4/1999 | Lobdell | B65D 35/36 222/192 |
| 6,074,210 | A * | 6/2000 | Garrison | A61C 5/88 433/149 |
| 6,976,842 | B1 * | 12/2005 | Miggantz | A61C 19/063 433/141 |
| 7,425,130 | B2 * | 9/2008 | Schaffner | A61C 5/88 433/149 |
| 8,419,427 | B2 * | 4/2013 | Effenberger | A61C 15/00 433/136 |
| 8,591,230 | B2 * | 11/2013 | Flanagan | A61C 19/04 433/80 |
| 8,734,154 | B2 * | 5/2014 | Effenberger | A61C 15/00 433/136 |
| 9,211,169 | B2 * | 12/2015 | Flanagan | A61C 19/04 |
| 2006/0283479 | A1 * | 12/2006 | Kernot | A61C 15/043 132/325 |
| 2010/0297575 | A1 * | 11/2010 | Effenberger | A61C 15/00 433/87 |
| 2011/0027753 | A1 * | 2/2011 | Maurat | A61C 9/0026 433/141 |
| 2018/0318055 | A1 * | 11/2018 | Lipp | A61C 19/063 |

* cited by examiner

*Primary Examiner* — Nicholas D Lucchesi
(74) *Attorney, Agent, or Firm* — Ira S. Dorman

(57) ABSTRACT

The device includes a wedge piece constructed for use in the non-surgical treatment of interproximal dental caries. A plunger is provided for driving substances through a passage in or on the wedge piece for enabling the delivery, to the site a carious lesion, of SDF or another substance that is effective for directly or indirectly killing, or biologically damaging, carious bacteria.

8 Claims, 3 Drawing Sheets

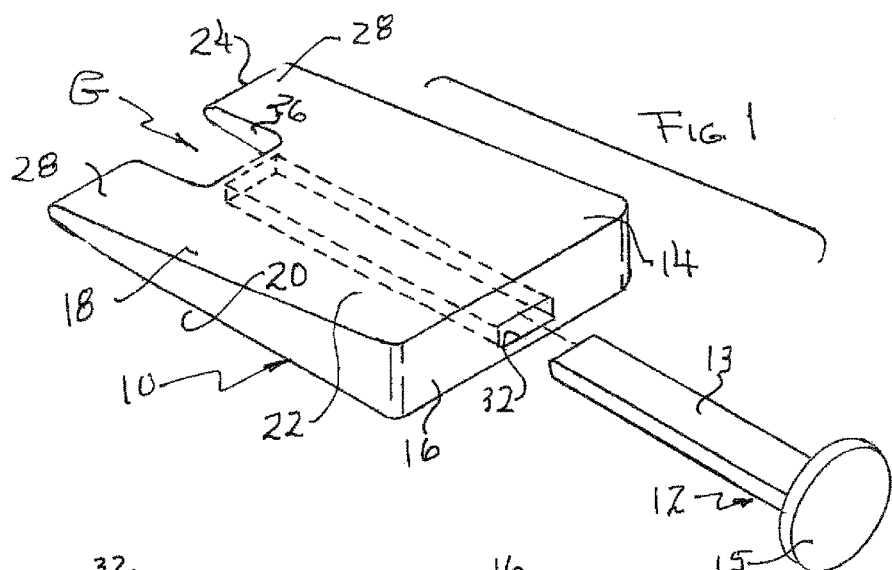
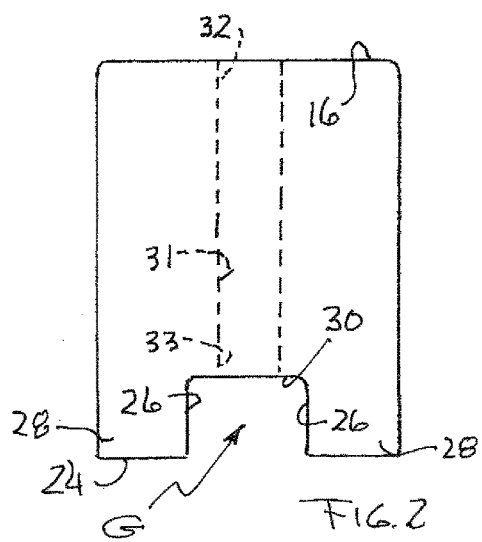
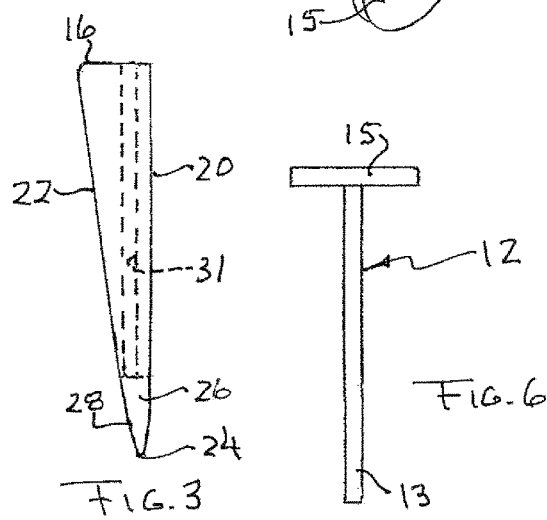
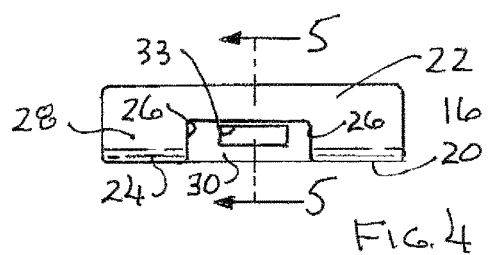
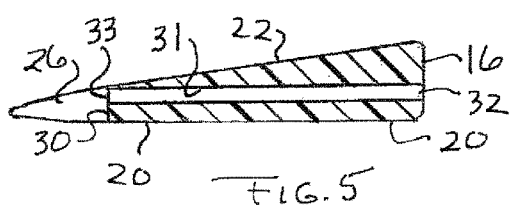

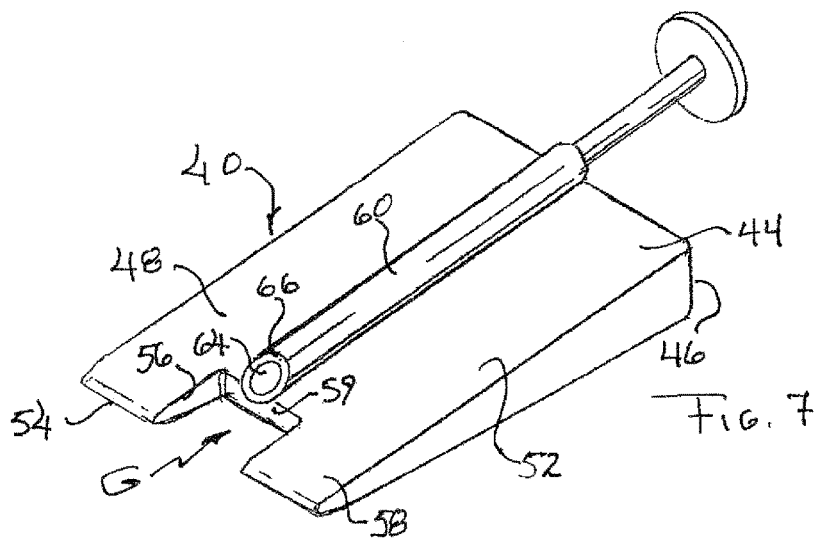
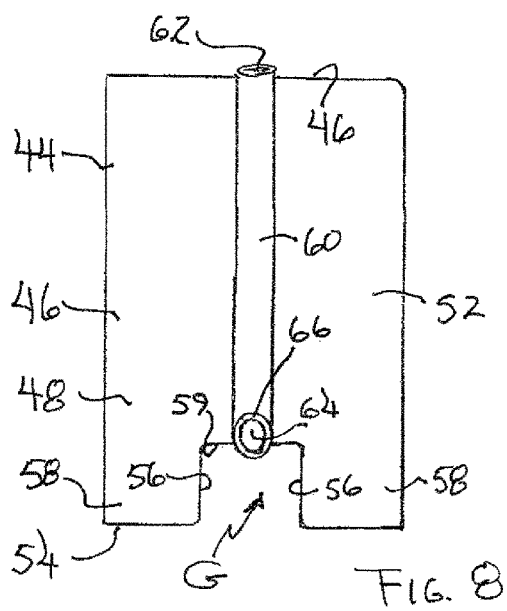 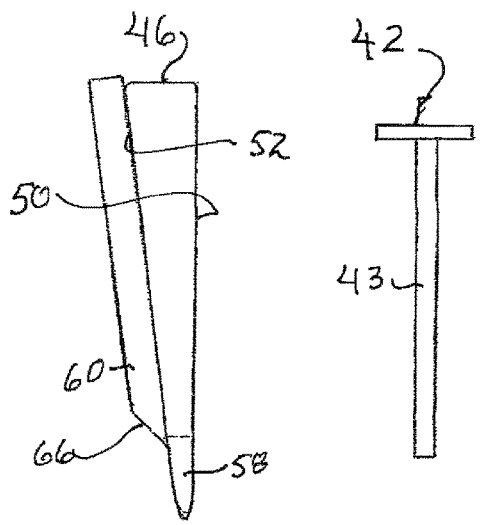 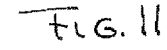
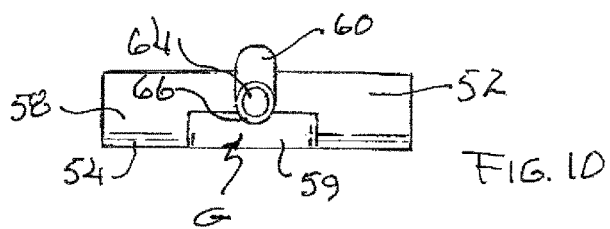

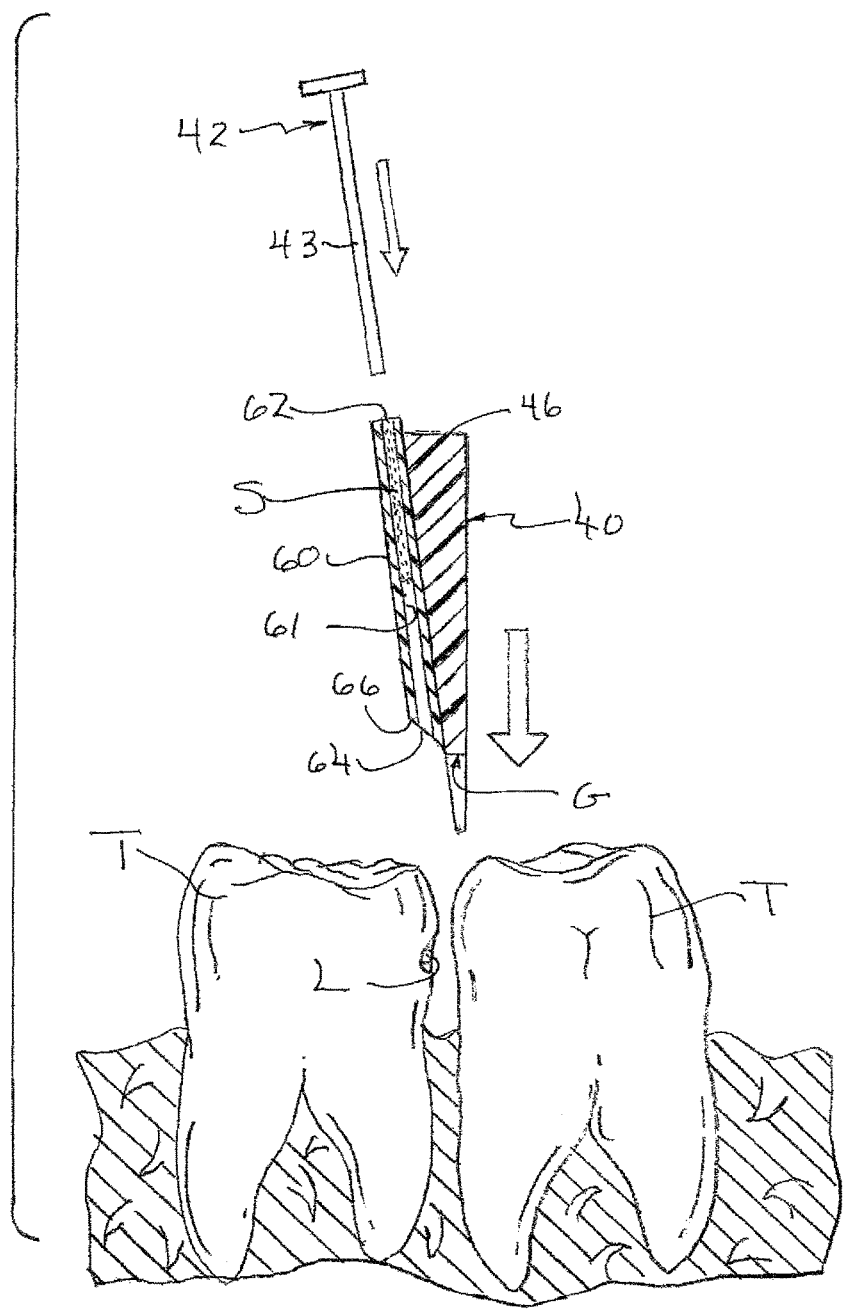

WEDGE DEVICE FOR FACILITATING TREATMENT OF INTERPROXIMAL DENTAL CARIES, AND METHOD OF USE

BACKGROUND OF THE INVENTION

Dental caries occur on all surfaces of teeth, and carious lesions can, and do, form between teeth in areas that are inaccessible directly for treatment; these are termed "interproximal" caries >or carious lesions. Because such caries are between the teeth, access generally requires the physical removal, with a dental-drill, of sound tooth structure over and/or proximate the carious lesion so as to, in turn, permit physical removal of the decay.

Carious bacteria can be entombed, or sealed, within conventional acrylic dental resins to thereby cause the death of the bacteria by isolating it from the source of its needed nutrients, i.e., food debris. But access to the carious lesion, to permit the application of such a seal, typically also requires the physical destruction of sound tooth structure.

Alternatively, carious bacteria can be entombed within deposits of laser-ablated tooth enamel and dentin. While any removal of sound tooth structure will usually be undesirable, enamel and dentin damaged by ablation can often be repaired by remineralization, through topical fluoride treatments. As yet another technique, carious bacteria can be killed by exposure to sufficient doses of microwave energy, to which tooth enamel is translucent. Laser beam radiation is also effective for killing carious bacteria directly.

Silver diammine fluoride (commonly spelled silver diamine fluoride, and known by the acronym "SDF") is recognized to be effective as a treatment for the prevention and arrest of dental caries. As indicated above, however, effective access to interproximal sites is difficult.

A device, comprised of a shim component, for effecting the delivery of substances directly to the sites of interproximal carious lesions is described and claimed in Flanagan U.S. Pat. No. 9,211,169. While effective for its intended purposes, the shim device of the Flanagan patent is not considered to be optimal for the delivery of SDF.

BRIEF SUMMARY OF THE DISCLOSURE

Accordingly, a broad object of the present invention is to provide a novel device for treating interproximal dental caries.

A more specific object is to provide such a device whereby treatment of interproximal dental caries can be effected without substantial destruction of sound tooth structure lying over, or located proximate to, a carious lesion.

Another object of the invention is to provide such a device which may include means for driving substances to the site of an interproximal carious lesion.

Additional objects of the invention are to provide such a device which is of incomplex and inexpensive construction, and which is facile and effective for use to treat interproximal dental caries.

Another broad object of the invention is to provide a novel, nonsurgical method for treatment of interproximal dental caries and, more particularly, for the effective delivery, to the sites of interproximal carious lesions, of silver diammine fluoride, or other like substance, for the arresting the progress of dental caries.

It has now been found that certain of the foregoing and related objects of the invention are attained by the provision of a device for treating interproximal dental caries, comprising a hard, rigid wedge piece including a body dimensioned and configured for insertion longitudinally between two adjacent teeth, the wedge piece body having a top portion at one end and a bottom portion, terminating in a bottom edge, at an opposite end. The bottom portion is indented to form a gap extending upwardly from the bottom edge, substantially on a longitudinal centerline of the wedge piece, and to define two leg elements extending along opposite sides of the gap. Structure of the wedge piece provides a generally longitudinal channel, or passage, that is disposed substantially on the centerline and having an entrance end proximate the top portion and an exit end proximate the bifurcation of the leg elements. The passage enables the delivery of a caries-treating substance from the top portion of the wedge piece to the gap.

Generally, the wedge piece comprising the device of the invention will have substantially planar opposite side surfaces extending along the length of the piece, with one of the side surfaces, or at least a bottom portion thereof, being slanted or inclined relative to the other. The longitudinal passage will normally be substantially rectilinear; it may be defined by structure within the wedge piece body or by structure (e.g., a tubular element) disposed on the body.

In most instances, the device of the invention will additionally include a plunger having a stem dimensioned and configured for being introduced into the entrance end of the passage, for slideable engagement therein. The plunger can thus function to drive a substance contained in the passage to the exit end thereof.

The wedge body will normally be fabricated from a hard, rigid synthetic resinous material (e.g., an acrylic plastic, nylon, Teflon, polycarbonate, etc.). The material of fabrication will be selected so as to substantially avoid chemical or other interaction with the substance that is to be delivered through the wedge piece passage, which will be a particularly significant factor when a strongly reactive substance, such as SDF, is to be employed.

Other objects of the invention are attained by the provision of a method for treating interproximal dental caries, which method comprises steps:

inserting the wedge piece hereinabove and hereinafter described between two adjacent teeth, with its bottom edge leading, at least one tooth of the pair having a carious lesion on an interproximal surface thereof;

adjusting the position of the wedge piece, as necessary, to substantially align the gap in the bottom portion of the body with the site of the carious lesion;

introducing into the entrance end of the wedge piece passage a treating substance that is effective to kill, or metabolically damage, carious bacteria and thereby arrest the progress of decay;

delivering the caries-treating substance to the exit end of the passage (normally using a plunger) and thereby to the gap between the leg portions and thus to the carious lesion site; and withdrawing the wedge piece from between the teeth. The caries-treating substance presently preferred is silver diammine fluoride.

BRIEF DESCRIPTION OF THE SEVERAL VIEWS OF THE DRAWINGS

FIG. 1 of the drawings is an exploded perspective view of a first embodiment of the device of the present invention, comprised of a wedge piece and a plunger.

FIGS. 2, 3, and 4 are plan, side elevational, and bottom end views, respectively, of the wedge piece body comprising the device of FIG. 1.

FIG. 5 is a sectional view of the wedge piece body, taken along line 5-5 of (i.e., the centerline of the body) of FIG. 4.

FIG. 6 is an elevational edge view of a plunger employed for driving a substance through the passage of the wedge piece body.

FIG. 7 is a perspective view of a second embodiment of the device of the present invention.

FIGS. 8, 9, and 10 are, respectively, plan, side elevational, and bottom end views of the wedge piece of the device of FIG. 7.

FIG. 11 is an elevational view of a plunger employed for driving a substance through the passage of a tubular element comprising the wedge piece of FIGS. 7 through 10.

FIG. 12 is a diagrammatic illustration showing the device of FIGS. 7 through 11 in use for treatment at the site of a carious lesion, the view being taken in section along line 12-12 of FIG. 8 (the longitudinal centerline of the wedge piece).

DETAILED DESCRIPTION OF THE INVENTION

Turning now in detail to FIGS. 1 through 6 of the appended drawings, the device illustrated comprises a downwardly tapered wedge body, generally designated by the number 10, and a plunger, generally designated by the numeral 12. The wedge body 10 is fabricated from a synthetic resinous material and has a top portion 14 at one end, providing a top surface 16, and a bottom portion 18 at the other end. A planar first side surface 20 is perpendicular to the top surface 16, and a planar opposite side surface 22 is disposed at an acute angle to the top surface 16 and thus is inclined relative to the first side surface 20 to impart a downward taper to the wedge body 10. It should be appreciated that only the bottom portion 18 the body need be tapered, albeit a taper along its entire length will usually be optimal.

The bottom portion 18 of the body 10 terminates in a bottom edge 24, which should be sufficiently narrow or sharp to facilitate insertion between proximal teeth. The edge 24 is indented at a central location to form an upwardly extending notch or gap, generally designated G, defined laterally by the interior surfaces 26 of a pair of leg elements 28 and upwardly by a bifurcating wall surface 30 between the leg elements. A passage 31 extends through the body 10 along its longitudinal centerline and generally parallel to the first surface 20, and opens at an entrance end 32 on the top surface 16 and at an exit end 33 (communicating with the gap G) on the wall surface 30. The stem portion 13 of the plunger 12 is of rectangular cross section for slidable receipt in the passage 31, with force on the head portion 15 being applied to promote movement of a substance through the passage.

The second embodiment of the device of the invention, illustrated in FIGS. 7 through 11, similarly comprises a downwardly tapered plastic wedge body, generally designated by the number 40, and a plunger, generally designated by the numeral 42. The wedge body 40 has a top portion 44 at one end, providing a top surface 46, and a bottom portion 48 at the other end. A planar first side surface 50 is perpendicular to the top surface 46, and a planar opposite side surface 52 is disposed at an acute angle to the top surface 46 and thus is inclined relative to the first side surface. Here again, only the bottom portion 48 the body 50 need be tapered.

As in the first embodiment described, the bottom portion of the body 40 terminates in a bottom edge 54, which is indented at a central location to form an upwardly extending gap G, defined laterally by the interior surfaces 56 of leg elements and upwardly by a wall surface 59.

In this embodiment of the invention (which will be preferred in many instances), rather than providing a passage through the body 40 (32 in the device of FIGS. 1 through 6) a tubular element or structure 60 is attached to the surface 52 of the body 40 on its longitudinal centerline. The structure 60 has a bore 61 (best seen in FIG. 12), providing a passage with an entrance 62 adjacent the top surface 46 of the body 40 and an exit 64 opening to the gap G, adjacent the defining upper wall surface 59. The cylindrical stem 43 of the plunder 42 is slidably received in the bore 61 of the tubular structure 60.

With particular reference to FIG. 12, and using the wedge device of FIGS. 7 through 11, as exemplary, for treatment at the site of the depicted interproximal carious lesion L, the body 40 is positioned for insertion between the adjacent teeth T and is forced downwardly (or upwardly, as the case may be) so as to spread the teeth slightly and bring the gap G to a position proximate the lesion L. The chamfered edge 66 at the exit end 64 of the tubular structure 60 facilitates insertion, and the leg elements 58 initiate the tooth-spreading action.

After insertion of the wedge body 40, a quantity of a substance S that is effective for treating the lesion L to arrest decay (e.g., SDF) is introduced into the bore 61 and forced by the plunger 42 to exit at 64, and thus to pass into the gap G and against the lesion L. The quantity of treatment chemical used may be minute because the surface of lesion L will typically be very small, and discharging an excessive amount of medicament at the treatment site will usually be undesirable.

After the treating substance has been delivered, the wedge piece will of course be removed from between the teeth. It will be appreciated that (albeit usually unnecessary) conventional wedges and other devices may be used to assist insertion and positioning of the instant wedge device, such as to preliminarily spread the teeth and/or depress or deflect gingival tissue, as will be evident to those skilled in the art.

As previously described, the wedge body will be constructed of any suitable hard, rigid material that is capable of being formed with a relatively sharp leading edge adapted for initiating entry between adjacent teeth, and that is suited for use for the delivery of a treating substance. Although, in the specific embodiments described and depicted, the wedge body is a slightly tapered (e.g., at about 5° to 10°), generally rectangular piece, it will be appreciated that substantial variations of shape may be incorporated without departure from the scope of the appended claims. For example, and as noted previously, the wedge piece body need not be tapered along its entire length, provided the bottom portion structure is sufficient to serve the purposes described; the lateral margins may converge toward one another and/or be non-linear; both side surfaces may be inclined relative to a central plane; and other modifications that will occur to those skilled in the art may be incorporated as well. Although the wedge body will typically be about 15 to 25 mm on a side (if rectangular), and about 1 to 2 mm thick (between its opposite side surfaces at the top end), it may of course have different dimensions; moreover, a single form of wedge may be provided in each of several sizes. The gap between the leg elements will typically extend across about one-third of the width of the body and along about one-fifth of its length.

The composition that will be desirable far fabrication of the wedge will, as indicated above, depend to an extent upon the nature of the substance that is to be used for treatment of the carious lesion, as will be evident to those skilled in the art in light of the present disclosure; for the delivery of SDF, an acrylic plastic will often be preferred. Any appropriate technique may be used to fabricate the wedges, including molding, punching, drilling, grinding, milling, etc. Due to the small cross-sectional dimensions of the passage, however, a most practical way to form it, within a wedge body, may involve the initial cutting of a slot, and then closing the slot by securing a strip of material on surfaces along its opposite sides.

Although the device of the invention will normally be employed for treating existing interproximal dental caries, it may be used, in appropriate circumstances, as a preventative measure for the delivery of medicaments to interproximal sites of prospective dental caries. It may also be employed for purposes other than killing of carious bacteria; e.g., for localized, interproximal topical fluoride treatment for purposes of remineralization.

Thus, it can be seen that the present invention provides a novel device for treating interproximal dental caries, which is of incomplex and inexpensive construction and is facile and effective for use for its intended purposes. Treatment can be effected without substantial destruction of sound tooth structure lying over, or located proximate to, a carious lesion. The invention also provides a novel method for treating interproximal dental caries, preferably using silver diammine fluoride as the treating substance.

Having thus described the invention, what is claimed is:

1. A device for treating interproximal dental caries, comprising a hard, rigid wedge piece including a body dimensioned and configured for insertion longitudinally between two adjacent teeth, said wedge piece body having a top portion at one end and a bottom portion, terminating in a bottom edge, at an opposite end, said bottom portion being indented to form a gap extending upwardly from said bottom edge, substantially on a longitudinal centerline of said wedge piece, and to define two leg elements, each leg element extending along an opposite side of said gap; structure of said wedge piece defining a generally longitudinal passage disposed substantially on said centerline of said wedge niece with an entrance end proximate said top portion and an exit end proximate the bifurcation of said leg elements, said passage enabling the delivery of a caries-treating substance from said top portion to said gap.

2. The device of claim 1 wherein said wedge piece has substantially planar opposite side surfaces extending along the length thereof, one of said side surfaces being inclined relative to the other.

3. The device of claim 2 wherein said longitudinal passage is substantially rectilinear, is contained substantially entirely within said wedge piece body, and extends substantially parallel to said other side surface.

4. The device of claim 1 wherein said longitudinal passage is substantially rectilinear and is contained substantially entirely within said wedge piece body.

5. The device of claim 1 wherein said passage-defining structure of said wedge piece comprises a tubular element disposed on said body.

6. The device of claim 1 additionally including a plunger having a stem dimensioned and configured for being introduced into said entrance end of said passage and for slideable engagement therein, whereby said plunger can function to drive a substance contained in said passage to said exit end thereof.

7. A method for treating interproximal dental caries, comprising the steps:
   - inserting said wedge piece of claim 1 between two adjacent teeth, with said bottom edge thereof leading, at least one of the adjacent teeth having a carious lesion on an interproximal surface thereof;
   - adjusting the position of said wedge piece, as necessary, to substantially align said gap in said bottom portion of said body with the site of the carious lesion;
   - introducing into said entrance end of said wedge piece passage a substance that is directly or indirectly effective to kill, or metabolically damage, carious bacteria;
   - delivering the substance to said exit end of said passage and thereby to said gap between said leg portions and thus to the carious lesion site; and
   - withdrawing said wedge piece from between the teeth.

8. The method of claim 7 wherein said substance is silver diammine fluoride.

* * * * *